United States Patent [19]

Stephan et al.

[11] Patent Number: 5,171,571
[45] Date of Patent: Dec. 15, 1992

[54] EFFERVESCENT TABLET

[76] Inventors: Dieter Stephan, Gehrenwaldstr. 35 A, 7000 Stuttgart, Fed. Rep. of Germany; Hans Honerlagen, Binsematt 2, 6314 Unterägri, Switzerland; Jochen Mitschka, Strünkerhof 13 a, 5303 Much; Günter Stephan, Happoldstr. 47, 7000 Stuttgart 30, both of Fed. Rep. of Germany

[21] Appl. No.: 671,756
[22] PCT Filed: Sep. 19, 1989
[86] PCT No.: PCT/EP89/01087
  § 371 Date: Apr. 23, 1991
  § 102(e) Date: Apr. 23, 1991
[87] PCT Pub. No.: WO90/03179
  PCT Pub. Date: Apr. 5, 1990

[30] Foreign Application Priority Data

Sep. 22, 1988 [DE] Fed. Rep. of Germany ....... 3822277

[51] Int. Cl.⁵ .................. A61K 35/78; A61K 9/46
[52] U.S. Cl. ................... 424/195.1; 424/466
[58] Field of Search ............. 424/195.1, 466; 514/165

[56] References Cited

PUBLICATIONS

Rote Liste, 1988, Editio Contor, (Aulendorf/Württ., DE) abstract No. 05031, Zeller-Koptschzenerz--Dragees.
Dictionaire Vidal, 1988, 64 Auflage OVP, (Paris Fr.), Aspirime USPSA vitamine C tampanee efferv.

Primary Examiner—John W. Rollins
Attorney, Agent, or Firm—Fay, Sharpe, Beall, Fagan, Mininich & McKee

[57] ABSTRACT

It is known to produce effervescent tablets incorporating salicyl acid analgetics gained synthetically, and, if required, vitamin adjuvants. In order to avoid the disadvantages of synthetically manufactured salicyl acid in such effervescent tablets, namely the irritation of the gastric mucosas and the inhibition of thrombocyte aggregation, and simultaneously to bring about new fields of use for effervescent tablets, an effervescent tablet is suggested which has, as an analgesic agent forming salicyclic acid, a water-soluble plant extract of the salicis extract type (willow bark extract) with a high active substance content. Thus, a galenically appropriate administration form of these generally extremely hygroscopic extracts is obtained. In the effervescent tablet, high active substance quantities can be resorbed rapidly, the salicyl acid forming the final active substance only being formed in the liver.

9 Claims, No Drawings

EFFERVESCENT TABLET

BACKGROUND OF THE INVENTION

1. Field of the Invention:

The invention relates to an effervescent tablet as a carrier for an analgesic agent forming salicylic acid.

2. Description of the Related Art:

Effervescent tablets are frequently pharmaceutically used as carriers for water-soluble and/or hygroscopic agents for the purpose of administering them in liquid form. One of the main uses is the administration of relatively high doses of vitamin and mineral preparations. As is generally known, the effervescent tablet constitutes a galenic form, in order to make available an active substance in a form which is rapidly resorbed by the human body.

It is generally known (cf. specialist publications Acta Facultatis Pharmaceuticae, Vol. XXVII, 1975, pp. 7 to 24, particularly pp. 12 and 18, as well as Helwig "Moderne Arzneimittel", Wiss. Verlagsgesellschaft, Stuttgart, pp. 20/21 under "Aspirin ® plus C" and "Boxacin ®") to produce effervescent tablets using synthetically obtained analgesics. However, it is necessary to accept two important negative characteristics or effects of synthetically produced salicylic acid, namely a) the irritation of the (gastric) mucosas and
b) the inhibition of thrombocyte aggregation (reducing the blood clotting capacity).

In addition, pharmaceutics based on acetylsalicylic acid (ASS) are now generally known, which are conventionally administered as tablets or powders. In the same way as salicylic effervescent tablets, they have an acrid taste and a relatively high pH-value.

SUMMARY OF THE INVENTION

The main aim of the invention is to extend the range of use of effervescent tablets as carriers for analgesic active substances whilst eliminating the described disadvantages of the known salicylic acid tablets, and to bring about new fields of use for effervescent tablets.

According to the invention this aim is achieved in that the agent is a water-soluble plant extract of the salicis extract type (willow bark extract) with a high active substance content. This gives a galenically appropriate administration form of these generally extremely hygroscopic extracts. As effervescent tablets are dissolved for ingestion, due to the fact that their size plays little or no part, they can contain high extract/active substance quantities. It is particularly important that these high active substance quantities can be resorbed extremely rapidly, i.e. the effect sought by the ingestion is made available for the patient extremely rapidly (reaching the $C_{max}$ state). As a result of the uniform, fast resorption of relatively high active substance quantities, it is possible in the case of long-term treatment of patients to produce a uniform active substance level over a long period. At the same time, an administration form for natural products is obtained which is highly acceptable to a very wide spectrum of purchasers and patients. The decisive differences between the salicis extract and the active substance salicin as a natural product on the one hand and ASS (acetylsalicylic acid) as a synthetic substance are that salicin is a glycoside, i.e. the active substance salicylic acid is bound to a sugar molecule, which is only split off in the intestine, where the object salicylic acid is formed as an analgesic substance. Although in the case of ASS the salicylic acid is also formed in the intestine, the starting substance ASS has a completely different chemical structure, e.g. ASS does not contain a sugar molecule. The ASS quantity necessary for bringing about the analgesic action is higher and also ASS has the aforementioned negative, namely the mucosas-irritating influence on passing through the stomach as a result of its free acid group.

Thus, compared with known ASS analgesics, a highly concentrated salicis extract-containing effervescent tablet according to the invention has in particular the following advantages:

a. Although in the case of the extract salicis or the active substance salicin, as in the case of ASS, salicylic acid is the final active substance, it is only formed by various transformations of the glycoside in the intestine and resorption in the liver. Thus, the ASS-typical side effects on the mucosas do not occur in the case of salicis extract due to the formation of salicylic acid in the liver, while, although as a result of the transformation the action of the salicis extract occurs later than with ASS, it lasts for a longer period of time.

b. The pH-value of the salicis extract is lower than in ASS.

c. The salicis extract's bitterness is only minimal compared with the acrid taste of ASS.

d. The salicis extract is a natural product and such natural products are increasingly accepted in commerce when compared with synthetically produced pharmaceuticals.

e. As an effervescent tablet makes the active substance available in a form which is rapidly resorbed with the aim of a rapid start of the action, it constitutes the optimum galenic form for the effect occurring later in the case of the salicis extract than with ASS, whilst the action lasts for a longer time, i.e. it combines the said advantages and disadvantages in an ideal form.

f. As the salicis extract with the high salicin content is highly hygroscopic, and as effervescent tablets also have this property, an effervescent tablet constitutes a preferred carrier form for it.

DETAILED DESCRIPTION OF THE PREFERRED EMBODIMENTS

Advantageously the salicis extract contains approximately 3 to 20 and preferably 7.5% by weight salicin. It is therefore possible to have a much lower salicin dose. Thus, in the case of ASS, the drug quantity for obtaining the sought analgesic action is 250 to 500 mg, whereas the salicin may be dosed at only 40 to 120 mg.

Furthermore, it is possible for the effervescent tablet to additionally contain a water-soluble component of a vitamin C product, preferably an extract of Acerola and lemon, so that, in addition to the mainly-sought analgesic action, the body is supplied with further antibodies in a pharmacologically appropriate manner.

The advantages attainable with the invention reside in that, through the choice of effervescent tablets as carriers for natural products on the one hand, the possibility of replacing synthetic medicaments in a particularly acceptable administration form is provided, whilst on the other hand the side-effects of such synthetic products are eliminated by moving the transformation processes to different points in the human body and longer or more durable effects are obtained, which in return reduces the dosage requirements. It must further be stressed, with particular regard to ASS products, that, following several studies, it has been found (cf. e.g.

Medizinische Monatsschrift für Pharmazeuten, 7/1988, pp. 230–232; Pharmazeutische Zeitung, No. 15, 1988, pp. 9–13) that the regular administration of such products reduces the myocardial infarction risk by 47%, but the tests had to be broken off in the case of approximately 30% of the test persons due to problems in the gastro-intestinal tract. This disadvantage is obviated by the use of willow bark extract because, as stated, the salicylic acid is only formed in the liver.

EXAMPLE

Several batches of effervescent tablets were produced with the following formulation:

| | |
|---|---|
| Salicis Sicc. extract | 800 mg |
| Sodium hydrogen carbonate | 900–1050 mg |
| Anhydrous citric acid | 1650–1750 mg |
| Polyethylene glycol 6000 | 480–520 mg |
| Sweetener (Aspartame, Cyclamate) | 60–80 mg |
| Lemon flavor | 60–80 mg |
| Polyvinyl pyrrolidone | 200–250 mg |

Average total tablet weight: 4400 mg

| | |
|---|---|
| Appearance: | beige-brown, circular tablets |
| Thickness: | 6.4–6.8 mm |
| Hardness, kg: | 2.5–4 |
| Dissolving time: | under 7 minutes |
| Taste: | sourish |
| Appearance of solution: | slightly cloudy, frothy |
| Salicin content: | 60 mg/tablet |

Production procedure

1. All the active substances and adjuvants are sieved through a Freiwitt sieve with a mesh size of 1.5 mm.
2. The sweetener, flavoring agent and polyvinyl pyrrolidone are homogeneously mixed in a laboratory mixer.
3. The salicis extract, sodium hydrogen carbonate, citric acid and polyethylene glycol 6000 are weighed and introduced into a Rhönrad mixer. The mixture from 2 is now added and mixed for 15 minutes. The homogeneity of the mixture is checked visually.
4. The tablets are compressed directly from the mixture.

What is claimed is:

1. An effervescent tablet as a carrier for an analgesic agent forming salicylic acid, wherein the agent is an extract of the willow bark (cortex salicis) type having a high active substance content.

2. An analgesic tablet with an extract of the willow bark (cortex salicis) type as active substance, wherein the extract is compressed, in the galenic form of an effervescent tablet, as a water-soluble substance in a mixture with an also easily water-soluble, gas developing and releasing carrier substance containing a binding agent, as well as with aromatic substances.

3. An analgestic tablet as claimed in claim 2, wherein the salicis extract contains approximately 3 to 20% by weight of salacin.

4. An analgesic tablet as claimed in claim 3, wherein the salicis extract contains 7.5% by weight of salacin.

5. An analgesic tablet as claimed in claim 2, wherein the salicis extract contains 7.5% by weight of salacin.

6. An analgesic tablet as claimed in claim 5, wherein the tablet additionally contains a water-soluble component of a vitamin C product.

7. An analgesic tablet as claimed in claim 2, wherein the tablet additionally contains a water-soluble component of a vitamin C product.

8. An analgesic tablet as claimed in claim 3, wherein the tablet additionally contains a water-soluble component of a vitamin C product.

9. An analgesic tablet as claimed in claim 2, wherein the vitamin C component is an extract of Acerola and lemon.

* * * * *